US00PP17135P3

(12) United States Plant Patent
McGranahan et al.

(10) Patent No.: US PP17,135 P3
(45) Date of Patent: Oct. 10, 2006

(54) WALNUT TREE NAMED 'GILLET'

(50) Latin Name: *Juglans regia*
Varietal Denomination: Gillet

(75) Inventors: Gale McGranahan, Davis, CA (US); Charles Leslie, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 159 days.

(21) Appl. No.: 10/944,025

(22) Filed: Sep. 17, 2004

(65) Prior Publication Data

US 2006/0031972 P1 Feb. 9, 2006

Related U.S. Application Data

(63) Continuation-in-part of application No. 10/912,781, filed on Aug. 6, 2004, now abandoned.

(51) Int. Cl.
*A01H 5/00* (2006.01)

(52) U.S. Cl. ..... Plt./154

(58) Field of Classification Search ..... Plt./154

See application file for complete search history.

*Primary Examiner*—Anne Marie Grunberg
*Assistant Examiner*—June Hwu

(74) *Attorney, Agent, or Firm*—Morrison & Foerster LLP

(57) ABSTRACT

A new and distinct variety of walnut tree denominated 'Gillet' is described. This new cultivar comes into bearing young, produces well mid-season, and bears a jumbo sized nut with light colored kernels of uniform size. The new cultivar can be harvested prior to 'Chandler' and furthermore shows low susceptibility to walnut blight.

7 Drawing Sheets

FIELD OF THE INVENTION

Botanical/commercial classification: (*Juglans regia*)/new English walnut variety. Varietal denomination: cv. Gillet.

BACKGROUND OF THE INVENTION

The present invention relates to a new and distinct variety of walnut tree *Juglans regia* which has been denominated varietally as 'Gillet,' and more particularly to such a walnut tree which has a harvest date approximately two weeks earlier than the walnut tree variety 'Chandler' (U.S. Plant Pat. No. 4,388) and which further produces a walnut that is jumbo in size with light colored kernels and which can be processed in shell or cracked.

It has long been recognized as desirable to provide walnut trees bearing large crops which are ripe for commercial harvesting and shipment midseason and exhibit low susceptibility to walnut blight. The tree of the present variety, 'Gillet,' produces a nut which is similar in some respects to common walnut tree varieties such as 'Chandler,' (U.S. Plant Pat. No. 4,388). However the new variety is ready for harvest approximately two weeks before 'Chandler,' and ten days after the common reference cultivar 'Payne' (not patented).

The new *Juglans regia* walnut tree of the present invention was created at Davis, Calif. in 1995 by a controlled cross of the cultivar 'Chico' and UC76-80 (neither patented). The pedigree is illustrated (FIG. 1).

Seeds from the cross were planted and the resulting 37 trees were carefully observed along with other trees in the walnut breeding program. When they began to bear nuts, data were collected annually on leafing date, first peak and last female flower bloom, first, peak and last male bloom, blight severity and yield (Table 1). Nuts were sampled, cracked, and data was collected on shell appearance, shell thickness, shell integrity, shell strength, nut weight, kernel weight, percent kernel, ease of kernel removal, kernel color, and percent kernel shrivel (Table 2). A single tree was selected from among progeny of this controlled cross based on its superior attributes. This selection was originally designated 'UC95-22-26,' and is now designated the 'Gillet' cultivar after Felix Gillet, a historical figure said to be responsible for introducing varieties suitable for the northern half of California and therefore responsible for the growth of the walnut industry early in the $20^{th}$ century. Compared to 'Gillet' the parent UC76-80 is protandrous and the nut has a weaker shell; the parent 'Chico' has smaller nuts than 'Gillet' with a more difficult to extract kernel.

The new cultivar of the present invention has been propagated by grafting at Davis, Calif. on 'Paradox' hybrid rootstock. The distinctive characteristics of the new cultivar have been found to be stable and are transmitted to the new trees when asexually propagated.

SUMMARY OF THE INVENTION

It was found that the new *Juglans regia* cultivar of the present invention exhibits the following combination of characteristics:

a) Comes into bearing young, with an excellent yield at age 3 years;
b) forms jumbo-sized walnuts that possess light-colored kernels with little size variation in a given harvest;
c) can be processed inshell or cracked;
d) bears fruit laterally;
e) yields a walnut crop that can be harvested 2 weeks prior to 'Chandler' (U.S. Plant Pat. No. 4,388).
f) is protogynous, bearing female flowers before male flowers; and
g) exhibits low susceptibility to blight.

BRIEF DESCRIPTION OF THE TABLES

Table 1 shows comparative tree evaluations.

Table 2 shows nut and kernel traits.

BOTANICAL DESCRIPTION OF THE PLANT

The description is based on an ungrafted walnut on its own roots and trees propagated by grafting on Paradox rootstock and growing in an orchard at Davis, Calif. Data were collected on the own rooted tree from 1999, at age 3 years, to 2003, age seven.

In 2002, scionwood from this tree was collected and grafted onto Paradox rootstock for further evaluation in three sites: Davis, Chico and Kearney.

The Munsell Book of Color is used in the identification of color. Also, common color terms are to be accorded their ordinary dictionary significance.

Botanical classification: *Juglans regia.*
*Female parent.*—'Chico'.
*Male parent.*—UC76-80.

Figure 1:
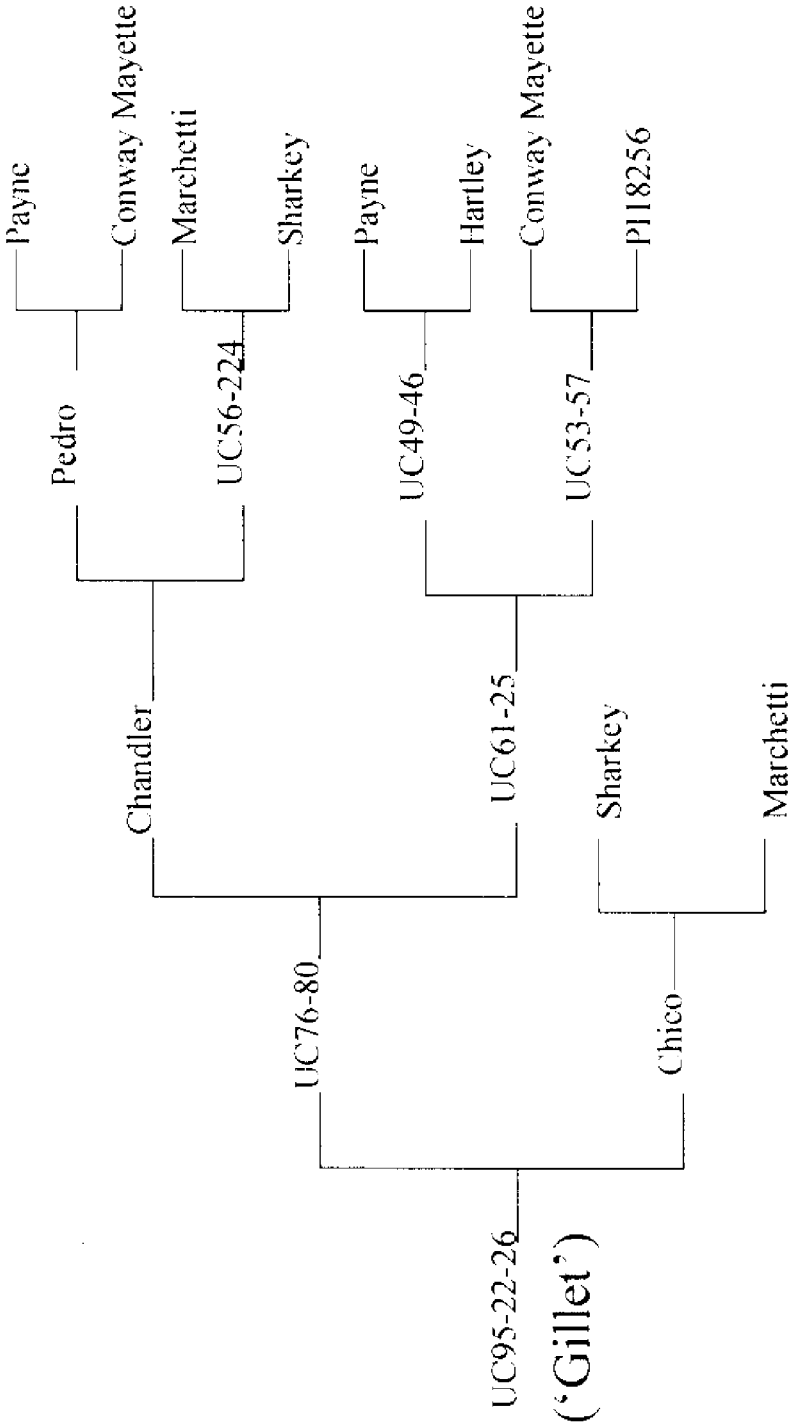
FIG. 1—shows the pedigree of the 'Gillet' walnut.

The pedigree is shown (FIG. 1).

Figure 2:
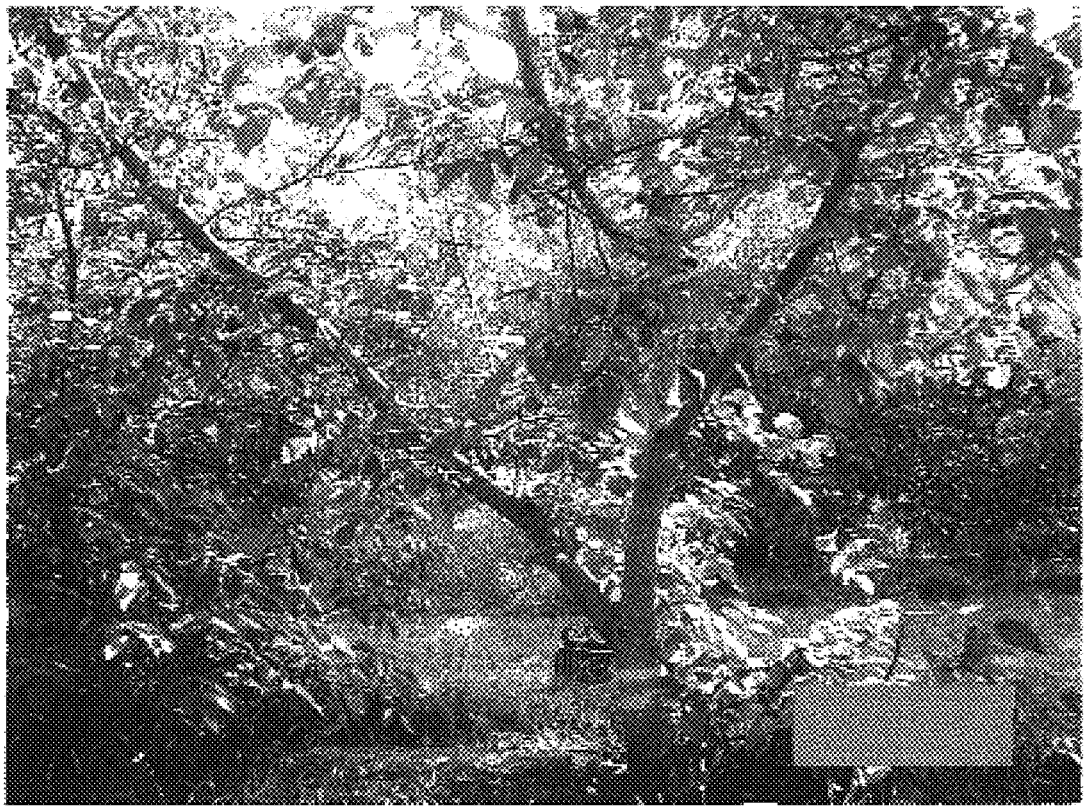
FIG. 2—shows a tree of the 'Gillet' walnut at seven years.
Figure 3:
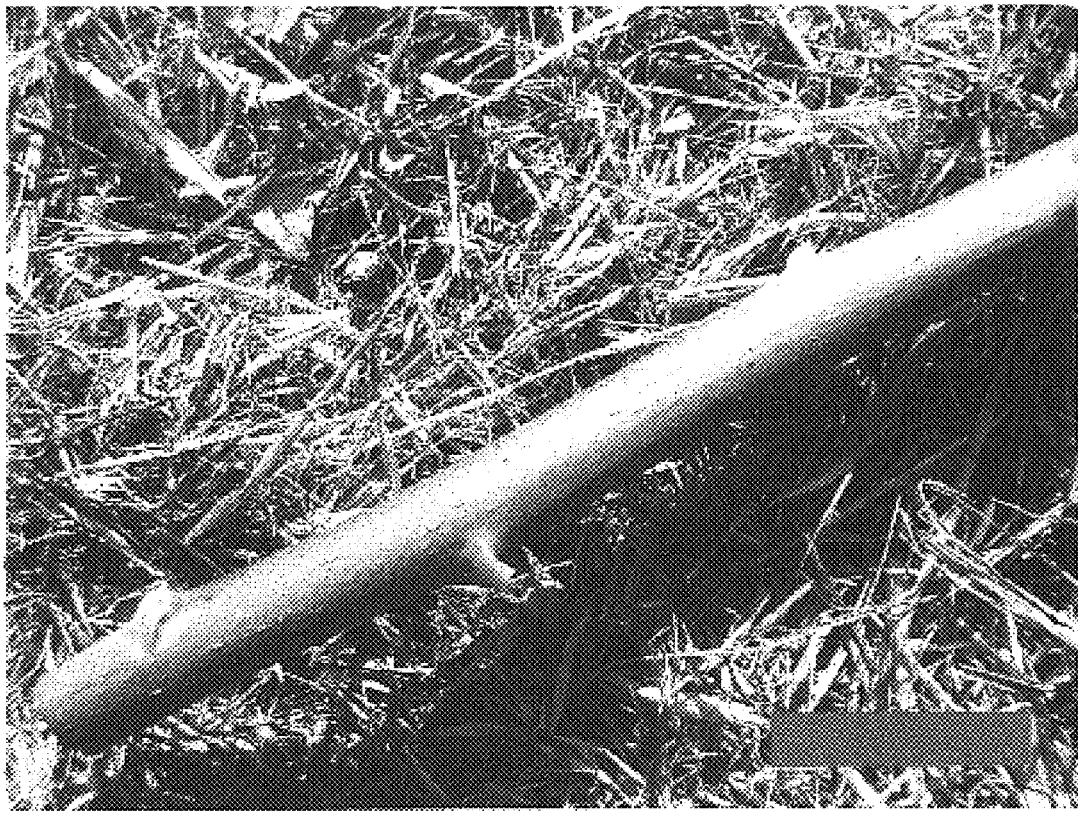
FIG. 3—shows a near view of the typical current season's stem of the 'Gillet' walnut.

Plant: The growth habit of the tree is illustrated in FIG. 2. This 7 year old tree was approximately 22 feet in height with a canopy diameter of approximately 19 feet. The trunk diameter at 30 cm above the ground is approximately 20 cm. The silvery grey bark is typical of *Juglans regia.* The young bark is brown (2.9GY 2.3/3.6) with raised white lenticels (FIG. 3) and the older bark is grey (5Y 7.5/2) with lighter striations (7 YR 8/2). On one-year-old bark there are about 12 lenticels per 2.5 cm of stem measuring approximately 1.5 cm in diameter. 'Gillet's lenticels are oval, measure 2–10 mm by 1–2 mm and are light grey yellow brown (9.7YR 4.6/2.1). 'Gillet' has vigor similar to the 'Serr' variety. The surface texture of trunk branch, leaflets, hull and kernel are smooth.

Figure 4:
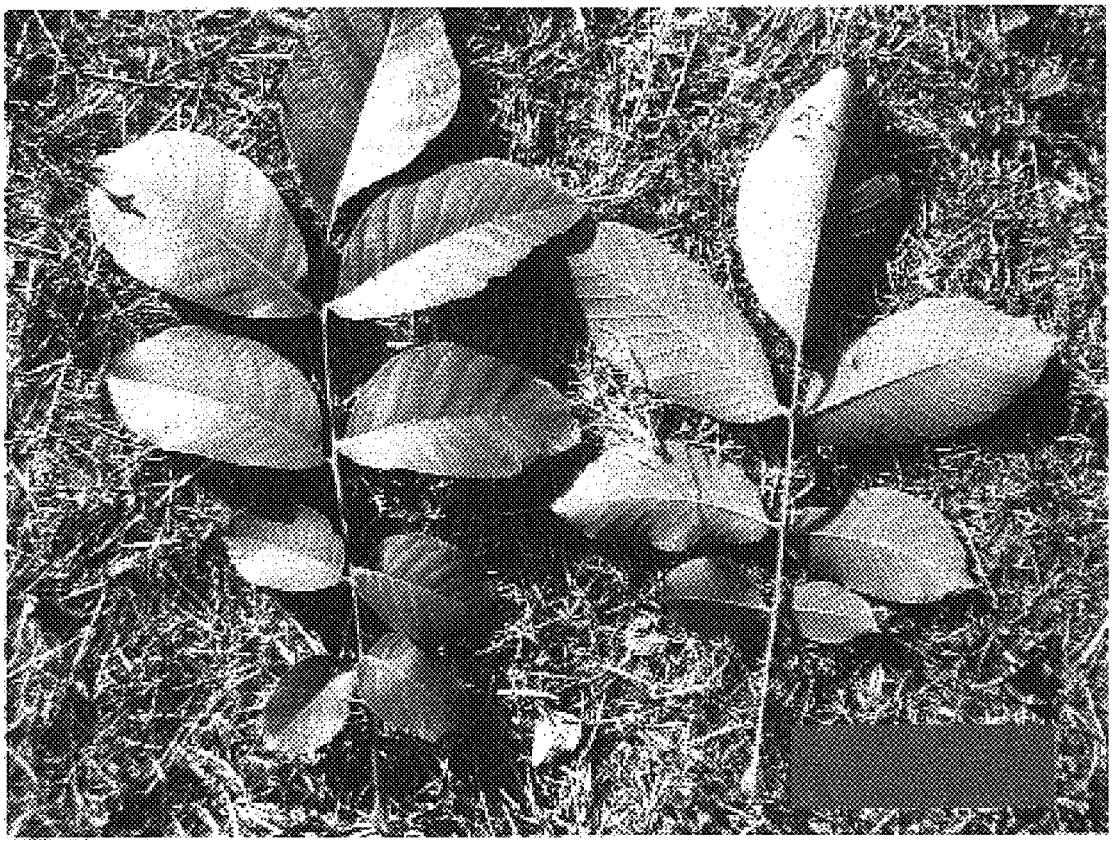
FIG. 4—shows a near view of the leaves of the 'Gillet' walnut.
Figure 5:
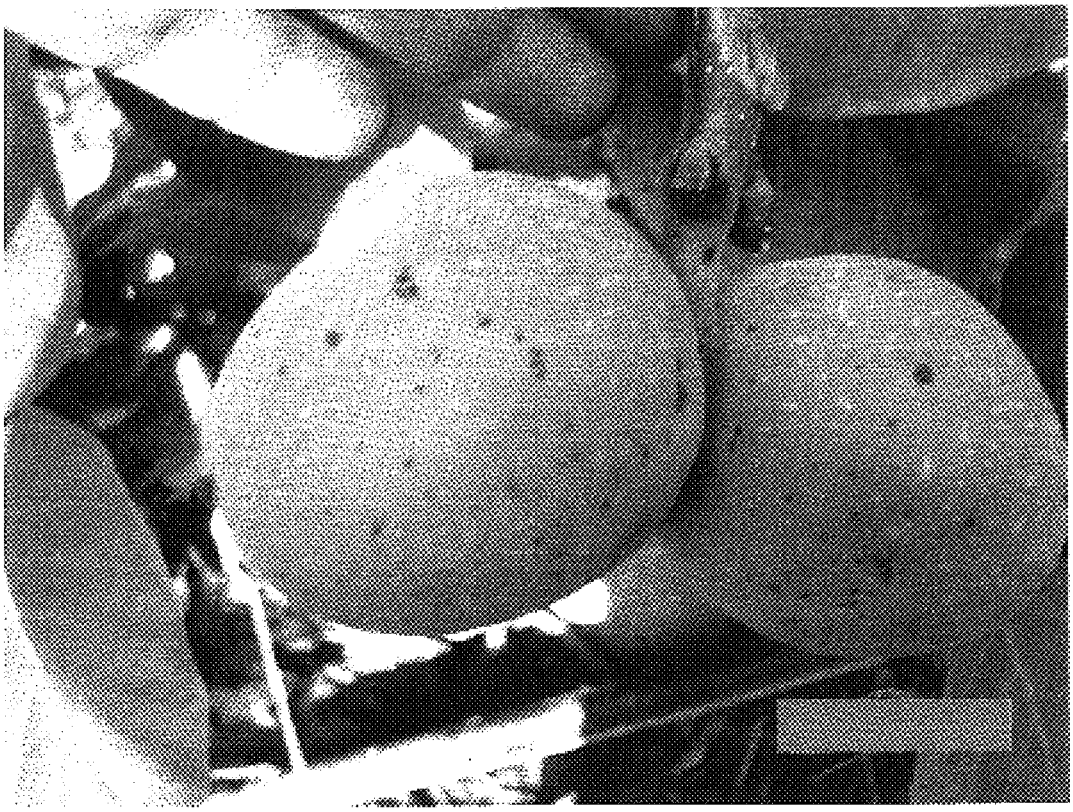
FIG. 5—shows a near view of the nuts in the hull of the 'Gillet' walnut just prior to maturity.
Figure 6:
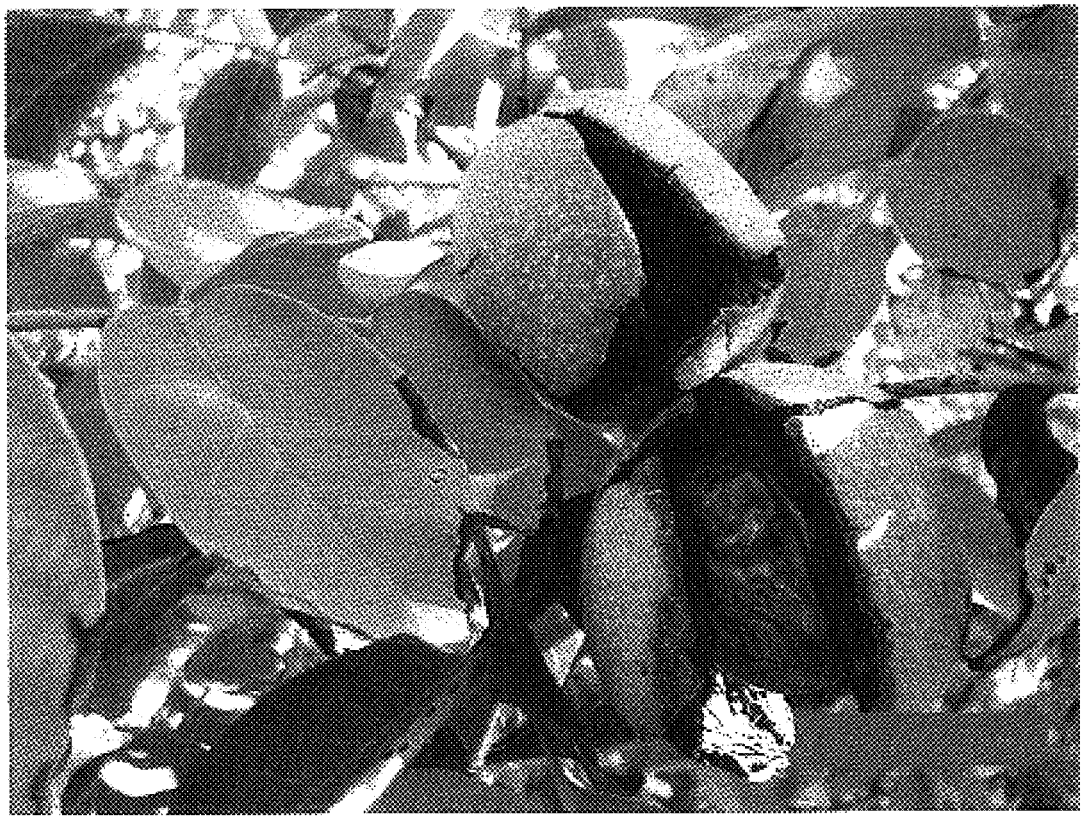
FIG. 6—shows nuts in the hull of the 'Gillet' walnut at maturity.
Figure 7:
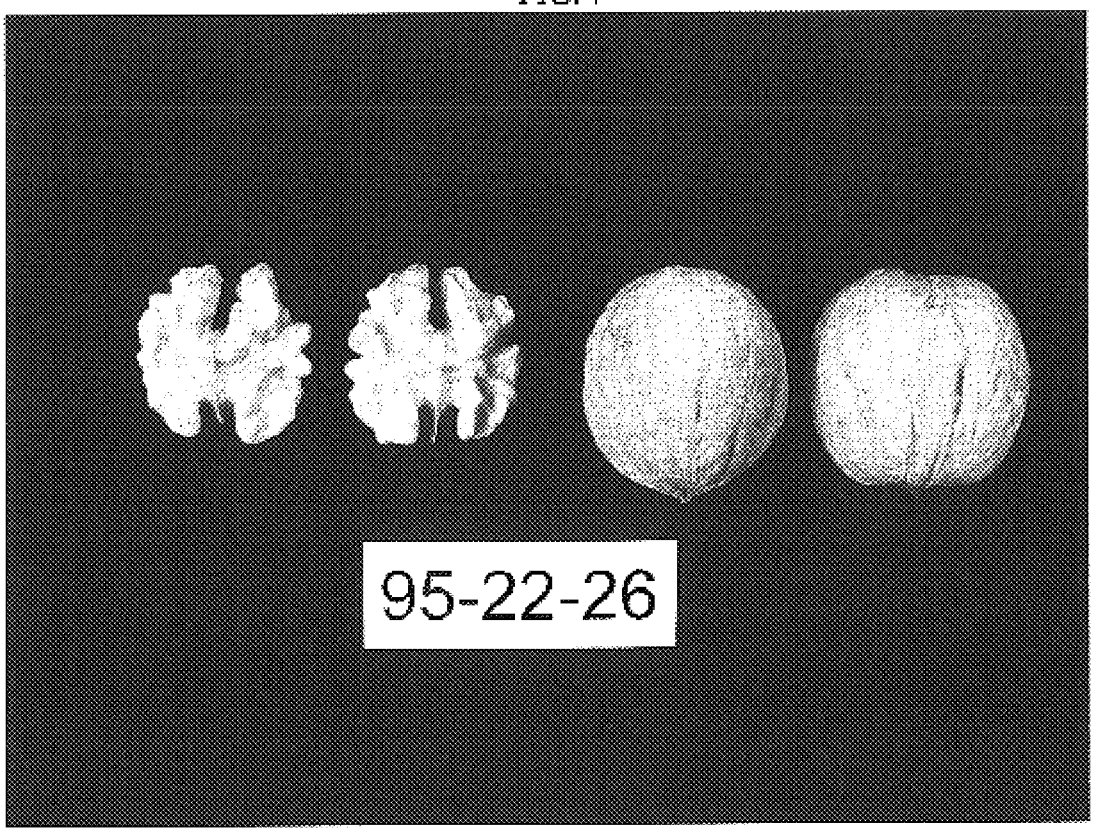
FIG. 7—shows kernel and nut of the 'Gillet' walnut.

Foliage: The dark green foliage is illustrated (FIG. 4) and is typical of *Juglans regia.* Leaf out during 1994–2003 has occurred on March 30 on the average. For comparative purposes the 'Payne' cultivar leafed out 9 days earlier and the 'Chandler' cultivar leafed out 7 days later during the same years. The typical leaf coloration is green, 6.1GY 3.2/5.8, on the upper surface, and slightly lighter (5.0GY 4.5/8.2) on the lower surface. The leaves are pinnately compound with 5–7 (9) leaflets. The full leaf length is approximately 37 cm and the width 26.6 cm. Leaflets are broadly elliptical and entire. The terminal leaflet averages 15 cm in length and 10 cm in width. The middle leaflets average 13 cm in length and 7.6 cm in width and the proximal leaflets average 8.9 cm in length and 5.4 cm in width. If 7 leaflets are present the first (proximal) set is smallest averaging 6.3 cm in length and 4 cm in width. The rachis averages 22.4 cm in length and is 1–2 mm in diameter. Petioles average length is 7 cm, 2–4 mm in diameter and 5GY 7/8 in color.

Inflorescence: The tree is relatively precocious, an excellent yield being noted at age 3 years. Male flowers (catkins) were not present until age 5. This delay in male maturity is typical of *Juglans regia.* The catkin's diameter is about 15 mm and yellow-green (5GY 6/8). Catkin length ranges between 7 and 13 cm. From 1999 to 2003, first female bloom occurred on an average on April 4, peak bloom on April 8 and last bloom on April 15. From 2001 to 2003, average male flowering (pollen shedding) began April 10, peaked on April 18 and terminated April 27. In this protogynous tree, pollen shedding does not completely cover pistillate bloom suggesting that a pollenizer would be needed for maximum yield in isolated areas. Both 'UC90-31-10' (patent application No. 10/912,852) and 'Serr' (unpatented) would be satisfactory pollenizers. The female flowers are typical of *Juglans regia* with two flowers per inflorescence borne at both terminal and lateral positions on current season's growth. Approximately 98% of the lateral buds contain inflorescences making yields much greater than trees that only bear flowers terminally. A typical female flower is approximately 5 to 7 mm at anthesis and the floral organs are typical of *J. regia.* The flowers appear vase-shaped when the two plumose stigmatic arms are curved outwardly. There are no petals. The flowers measure 5–7 mm in length and 3–5 mm in diameter and are yellow-green (5GY 6/8) in color. They are borne usually in twos on a 1 cm spike. The flower fragrance is typical of *J. regia* and is not noticeably different than the foliage fragrance.

Walnuts: The new cultivar commonly harvests at least eleven days before 'Chandler' and two weeks after 'Payne' but may become earlier as the clone ages. During 2003, nuts of this new cultivar were ready for harvest on October 1. This compares with 'Payne' that harvested September 21, and 'Chandler' that harvested October 19. The new cultivar has excellent yields of jumbo-sized walnuts. The hull is globose, 5 cm×5 cm, 5.8 mm thick and 2.5GY 8/6 in color. The apex is between rounded and truncate, the base is round and it is approximately 1.3–1.5 mm thick. The round nutshell is tan, relatively smooth, and measures approximately 38.7 mm in length and 38.5 mm in width. The shell is strong and well sealed and the kernel is easy to remove. The kernel weighs 8.2 g and makes up 51.5% of the total nut weight of 16.0 g. Kernel color is considered excellent and scores mostly in the light to extra light categories of the USDA Standards for Grades of Shelled Walnuts as determined by using the standard Walnut Color Chart for kernels published by the Dried Fruit Association of California. In addition kernels of 'Gillet' scored 55 on the Relative Light Index used by Diamond Walnut of Stockton, Calif. These values are based on 5 year averages of ten walnut samples obtained each year from a young tree. Typical kernel dimensions are approximately 31.8 mm in length and 32.3 mm in width. The kernel is essentially round and splits into halves easily. It is plump in comparison to 'Chandler'. It is typical of commercial walnuts in terms of flavor and firmness, the latter varying according to the percent moisture after drying.

Hardiness: The non-bearing tree withstood a temperature of 21° F. in 1998.

Chilling requirement: Trees have not shown staggered leafing and bloom, symptoms of lack of chilling when exposed to over 767 chilling hours (hours under 45° F.).

Disease resistance and susceptibility: Susceptibility to walnut blight has been low even though adjacent trees have been severely afflicted. No other unusual resistance or susceptibility to insects and diseases has been observed to date.

Usage: The new cultivar of the present invention provides a mid-season harvesting walnut cultivar with light colored kernels that can be used cracked or in shell.

TABLE 1

TREE EVALUATIONS

| | Leafing date | DAP L | Male bloom date | DAP M | Female bloom date |
|---|---|---|---|---|---|
| 1999 | | | | | |
| Payne | 3/24 | 0 | 4/14 | 0 | 4/18 |
| Tulare | 4/10 | 17 | 4/17 | 3 | 4/25 |
| Chandler | 4/13 | 20 | 4/17 | 3 | 4/28 |
| Sexton | 4/6 | 13 | 4/18 | 4 | 4/19 |
| Gillet | 4/11 | 18 | | | 4/22 |
| Forde | 4/14 | 21 | | | 4/23 |
| 2000 | | | | | |
| Payne | 3/19 | 0 | 3/31 | 0 | 4/5 |
| Tulare | 4/3 | 15 | 4/11 | 11 | 4/15 |
| Chandler | 4/4 | 16 | 4/12 | 12 | 4/20 |
| Sexton | 3/28 | 9 | 4/5 | 5 | 4/10 |
| Gillet | 3/30 | 11 | | | 4/7 |
| Forde | 4/3 | 15 | | | 4/10 |
| 2001 | | | | | |
| Payne | 3/17 | 0 | 3/27 | 0 | 4/1 |
| Tulare | 3/29 | 12 | 4/10 | 13 | 4/20 |
| Chandler | 3/29 | 12 | 4/10 | 13 | 4/23 |
| Sexton | 3/22 | 5 | 3/26 | 0 | 4/7 |
| Gillet | 3/23 | 6 | 4/15 | 18 | 3/30 |
| Forde | 3/24 | 7 | 4/15 | 18 | 4/3 |
| 2002 | | | | | |
| Payne | 3/27 | 0 | 4/6 | 0 | 4/12 |
| Tulare | 4/6 | 10 | 4/15 | 9 | 4/24 |
| Chandler | 4/7 | 11 | 4/17 | 11 | 4/27 |
| Sexton | 4/1 | 5 | 4/10 | 4 | 4/15 |
| Gillet | 4/1 | 5 | 4/23 | 17 | 4/11 |
| Forde | 4/2 | 6 | 4/23 | 17 | 4/13 |
| 2003 | | | | | |
| Payne | 3/18 | 0 | 4/5 | 0 | 4/9 |
| Tulare | 4/5 | 18 | 4/18 | 13 | 4/26 |
| Chandler | 4/7 | 20 | 4/20 | 15 | 5/3 |
| Sexton | 3/24 | 6 | 4/5 | 0 | 4/9 |
| Gillet | 3/24 | 6 | 4/18 | 13 | 4/4 |
| Forde | 3/27 | 9 | 4/23 | 18 | 4/9 |
| 5 YEAR AVERAGE | | | | | |
| Payne | 3/21 | 0 | 4/4 | 0 | 4/9 |
| Tulare | 4/4 | 14 | 4/14 | 10 | 4/22 |
| Chandler | 4/7 | 16 | 4/15 | 11 | 4/26 |
| Sexton | 3/29 | 8 | 4/6 | 2 | 4/12 |
| Gillet | 3/30 | 9 | 4/19 | 16 | 4/8 |
| Forde | 4/1 | 11 | 4/20 | 18 | 4/12 |

TABLE 1-continued

TREE EVALUATIONS

| | DAP F | Harvest Date | DAP H | Season length | Overlap % |
|---|---|---|---|---|---|
| 1999 | | | | | |
| Payne | 0 | 9/24 | 0 | 159 | 89 |
| Tulare | 7 | 10/5 | 11 | 166 | 27 |
| Chandler | 10 | 10/19 | 25 | 174 | 53 |
| Sexton | 1 | 10/1 | 7 | 165 | 88 |
| Gillet | 4 | 10/10 | 16 | 171 | |
| Forde | 5 | 10/22 | 28 | 182 | |
| 2000 | | | | | |
| Payne | 0 | 9/13 | 0 | 161 | 89 |
| Tulare | 10 | 10/3 | 20 | 172 | 100 |
| Chandler | 15 | 10/12 | 29 | 175 | 67 |
| Sexton | 5 | 9/30 | 17 | 173 | 54 |
| Gillet | 2 | 9/26 | 13 | 172 | |
| Forde | 5 | 10/7 | 24 | 180 | |
| 2001 | | | | | |
| Payne | 0 | 9/9 | 0 | 161 | 89 |
| Tulare | 20 | 9/27 | 15 | 160 | 85 |
| Chandler | 22 | 10/7 | 28 | 167 | 38 |
| Sexton | 6 | 9/29 | 20 | 175 | 53 |
| Gillet | −2 | 9/18 | 9 | 172 | |
| Forde | 2 | 9/29 | 20 | 179 | |
| 2002 | | | | | |
| Payne | 0 | 9/18 | 0 | 159 | 60 |
| Tulare | 12 | 10/3 | 16 | 162 | 91 |
| Chandler | 15 | 10/9 | 21 | 165 | 75 |
| Sexton | 3 | 10/3 | 15 | 171 | 83 |
| Gillet | −1 | 10/4 | 16 | 176 | 40 |
| Forde | 1 | 10/6 | 18 | 176 | 11 |
| 2003 | | | | | |
| Payne | 0 | 9/21 | 0 | 165 | 62 |
| Tulare | 17 | 10/5 | 14 | 164 | 92 |
| Chandler | 25 | 10/10 | 19 | 160 | 50 |
| Sexton | 0 | 10/6 | 15 | 180 | 100 |
| Gillet | −5 | 10/1 | 10 | 180 | 42 |
| Forde | 0 | 10/3 | 12 | 177 | 20 |
| 5 YEAR AVERAGE | | | | | |
| Payne | 0 | 9/17 | 0 | 161 | 78 |
| Tulare | 13 | 10/3 | 17 | 165 | 79 |
| Chandler | 17 | 10/11 | 24 | 168 | 57 |
| Sexton | 3 | 10/1 | 15 | 173 | 76 |
| Gillet | 0 | 9/30 | 13 | 174 | 41 |
| Forde | 3 | 10/7 | 20 | 179 | 15 |

| | Male abundance | Female abundance | Lateral fruitfulness % | Yield | Blight |
|---|---|---|---|---|---|
| 1999 | | | | | |
| Payne | 6 | 7 | 100 | 6 | 3 |
| Tulare | 4 | 6 | 90 | 6 | 0 |
| Chandler | 4 | 5 | 90 | 5 | 3 |
| Sexton | 6 | 7 | 100 | 7 | 2 |
| Gillet | | 5 | 90 | 5 | 0 |
| Forde | | 6 | 100 | 4 | 0 |
| 2000 | | | | | |
| Payne | 6 | 6 | 100 | 6 | 5 |
| Tulare | 6 | 6 | 100 | 6 | 4 |
| Chandler | 4 | 5 | 90 | 4 | 0 |
| Sexton | 5 | 6 | 100 | 6 | 0 |
| Gillet | | 6 | 100 | 6 | 0 |
| Forde | | 5 | 100 | 6 | 0 |
| 2001 | | | | | |
| Payne | 7 | 6 | 100 | 5 | 8 |
| Tulare | 6 | 6 | 70 | 5 | 3 |
| Chandler | 5 | 5 | 100 | 4 | 2 |
| Sexton | 5 | 6 | 100 | 6 | 1 |
| Gillet | 3 | 6 | 100 | 7 | 0 |
| Forde | 2 | 6 | 100 | 7 | 0 |
| 2002 | | | | | |
| Payne | 7 | 6 | 100 | 7 | 3 |
| Tulare | 5 | 6 | 100 | 6 | 0 |
| Chandler | 5 | 6 | 100 | 6 | 1 |
| Sexton | 6 | 6 | 100 | 6 | 0 |

TABLE 1-continued

| TREE EVALUATIONS | | | | | |
|---|---|---|---|---|---|
| Gillet | 4 | 6 | 100 | 6 | 0 |
| Forde | 4 | 6 | 100 | 6 | 0 |
| 2003 | | | | | |
| Payne | 5 | 6 | 100 | 6 | 7 |
| Tulare | 5 | 6 | 100 | 6 | 5 |
| Chandler | 4 | 6 | 100 | 4 | 0 |
| Sexton | 5 | 6 | 100 | 6 | 2 |
| Gillet | 6 | 6 | 100 | 7 | 1 |
| Forde | 4 | 6 | 100 | 7 | 2 |
| 5 YEAR AVERAGE | | | | | |
| Payne | 6.2 | 6.2 | 100 | 6 | 5.2 |
| Tulare | 5.2 | 6 | 92 | 5.8 | 2.4 |
| Chandler | 4.4 | 5.4 | 96 | 4.6 | 1.2 |
| Sexton | 5.4 | 6.2 | 100 | 6.2 | 1 |
| Gillet | 4.3 | 5.8 | 98 | 6.2 | 0.2 |
| Forde | 3.3 | 5.8 | 100 | 6 | 0.4 |

KEY TO TABLE 1

| | |
|---|---|
| Leafing date | Date when 50% of terminal buds have enlarged and the bud scales have split exposing the green leaves |
| DAP L | Days after Payne (reference cultivar) leafing |
| Male bloom date | Date when maximum pollen shedding occurs |
| DAP M | Days after Payne (reference cultivar) male bloom |
| Female bloom date | Date of maximum pistillate flower receptivity |
| DAP F | Days after Payne (reference cultivar) female bloom |
| Harvest Date | Date when 95% of the nuts separate from the hulls |
| DAP H | Days after Payne (reference cultivar) harvest |
| Season length | Days between female flowering and harvest |
| Overlap % | Percent of female bloom overlapped by male bloom |
| Male abundance | Male flower abundance: 3 low; 5 intermediate; 7 high |
| Female abundance | Female flower abundance: 3 low; 5 intermediate; 7 high |
| Lateral fruitfulness % | Percent of lateral buds with female flowers |
| Yield | Yield: 3 low; 5 intermediate; 7 high |
| Blight | Blight incidence: 3 low; 5 intermediate; 7 high |

DFA Dried Fruit Association of CA

TABLE 2

| NUT AND KERNEL TRAITS | | | | | | |
|---|---|---|---|---|---|---|
| | SHELL | | | | | |
| | Texture | Color | Seal | Strength | Integrity | Thickness |
| 1999 | | | | | | |
| Payne | 5 | 5 | 5 | 5 | 7 | 1.3 |
| Tulare | 5 | 6 | 4 | 4 | 7 | 1.2 |
| Chandler | 5 | 4 | 5 | 4 | 7 | 1.2 |
| Sexton | 5 | 5 | 6 | 6 | 7 | 1.5 |
| Gillet | 5 | 5 | 3 | 5 | 7 | 1.5 |
| Forde | 5 | 5 | 5 | 5 | 7 | 1.6 |
| 2000 | | | | | | |
| Payne | 5 | 5 | 5 | 5 | 7 | 1.4 |
| Tulare | 6 | 6 | 4 | 5 | 7 | 1.3 |
| Chandler | 5 | 5 | 5 | 4 | 7 | 1.4 |
| Sexton | 4 | 6 | 5 | 6 | 7 | 1.7 |
| Gillet | 6 | 5 | 4 | 4 | 7 | 1.3 |
| Forde | 8 | 5 | 4 | 5 | 7 | 1.2 |
| 2001 | | | | | | |
| Payne | 5 | 5 | 5 | 5 | 7 | 1.5 |
| Tulare | 5 | 6 | 5 | 4 | 7 | 1.3 |
| Chandler | 5 | 4 | 5 | 4 | 7 | 1.5 |
| Sexton | 4 | 5 | 5 | 5 | 7 | 1.6 |

TABLE 2-continued

| NUT AND KERNEL TRAITS | | | | | | |
|---|---|---|---|---|---|---|
| Gillet | 5 | 5 | 4 | 4 | 7 | 1.2 |
| Forde | 5 | 5 | 5 | 5 | 7 | 1.5 |
| 2002 | | | | | | |
| Payne | 5 | 5 | 5 | 5 | 7 | 1.0 |
| Tulare | 5 | 5 | 5 | 4 | 7 | 1.2 |
| Chandler | 5 | 4 | 5 | 5 | 7 | 1.5 |
| Sexton | 4 | 5 | 5 | 5 | 7 | 1.4 |
| Gillet | 5 | 5 | 4 | 5 | 7 | 1.3 |
| Forde | 5 | 4 | 5 | 5 | 7 | 1.5 |
| 2003 | | | | | | |
| Payne | 5 | 5 | 5 | 6 | 7 | 1.6 |
| Tulare | 5 | 6 | 5 | 4 | 7 | 1.2 |
| Chandler | 6 | 4 | 5 | 4 | 7 | 1.3 |
| Sexton | 4 | 5 | 5 | 5 | 7 | 1.5 |
| Gillet | 5 | 5 | 5 | 5 | 7 | 1.3 |
| Forde | 6 | 5 | 8 | 6 | 7 | 1.6 |
| 5 YEAR AVERAGE | | | | | | |
| Payne | 5 | 5 | 5 | 5.2 | 7 | 1.4 |
| Tulare | 5.2 | 5.8 | 4.8 | 4.2 | 7 | 1.2 |
| Chandler | 5 | 4.2 | 5 | 4.2 | 7 | 1.4 |
| Sexton | 4.2 | 5.2 | 5.2 | 5.4 | 7 | 1.5 |
| Gillet | 5.2 | 5 | 4 | 4.6 | 7 | 1.3 |
| Forde | 5.4 | 4.8 | 5 | 5.2 | 7 | 1.5 |

| | Packing tissue | Inshell weight | Kernel weight | Kernel % |
|---|---|---|---|---|
| 1999 | | | | |
| Payne | 5 | 18.9 | 5.3 | 44.9 |
| Tulare | 5 | 14.0 | 7.7 | 57.7 |
| Chandler | 5 | 13.7 | 7.1 | 52.2 |
| Sexton | 5 | 14.2 | 8.9 | 48.4 |
| Gillet | 5 | 18.5 | 8.2 | 49.8 |
| Forde | 5 | 18.8 | 9.7 | 51.7 |
| 2000 | | | | |
| Payne | 5 | 12.8 | 6.1 | 48.0 |
| Tulare | 5 | 16.4 | 9.2 | 58.5 |
| Chandler | 5 | 13.7 | 6.7 | 49.1 |
| Sexton | 5 | 17.0 | 8.6 | 50.7 |
| Gillet | 5 | 17.0 | 9.0 | 52.9 |
| Forde | 5 | 17.3 | 10.3 | 58.8 |
| 2001 | | | | |
| Payne | 5 | 15.4 | 7.4 | 48.2 |
| Tulare | 5 | 18.9 | 8.8 | 52.5 |
| Chandler | 5 | 15.0 | 7.5 | 49.7 |
| Sexton | 5 | 16.0 | 8.2 | 51.2 |
| Gillet | 5 | 15.0 | 8.1 | 53.8 |
| Forde | 5 | 15.1 | 8.0 | 53.0 |
| 2002 | | | | |
| Payne | 5 | 12.1 | 5.6 | 46.8 |
| Tulare | 5 | 15.0 | 8.2 | 55.0 |
| Chandler | 5 | 13.7 | 6.2 | 45.4 |
| Sexton | 5 | 18.5 | 9.9 | 53.4 |
| Gillet | 5 | 15.2 | 7.7 | 50.8 |
| Forde | 5 | 16.7 | 8.9 | 53.4 |
| 2003 | | | | |
| Payne | 5 | 15.6 | 7.4 | 47.1 |
| Tulare | 5 | 15.2 | 8.5 | 55.9 |
| Chandler | 5 | 13.6 | 7.1 | 51.1 |
| Sexton | 5 | 15.4 | 7.7 | 50.2 |
| Gillet | 5 | 16.2 | 8.2 | 50.5 |
| Forde | 5 | 17.6 | 9.1 | 51.7 |
| 5 YEAR AVERAGE | | | | |
| Payne | 5 | 14.8 | 6.4 | 47 |
| Tulare | 5 | 15.5 | 8.5 | 55.5 |

TABLE 2-continued

| NUT AND KERNEL TRAITS | | | | |
|---|---|---|---|---|
| Chandler | 5 | 14 | 6.9 | 49.5 |
| Sexton | 5 | 16.2 | 8.3 | 50.8 |
| Gillet | 5 | 16 | 8.2 | 51.6 |
| Forde | 5 | 17.1 | 9.2 | 53.7 |

| | KERNEL | | | | | |
|---|---|---|---|---|---|---|
| | Fill | Plumpness | Ease of removal | Blanks % | Extra light % | Light % |
| 1999 | | | | | | |
| Payne | 5 | 4 | 4 | 0 | 50 | 30 |
| Tulare | 5 | 5 | 4 | 0 | 0 | 100 |
| Chandler | 4 | 5 | 3 | 0 | 90 | 10 |
| Sexton | 5 | 5 | 4 | 0 | 100 | 0 |
| Gillet | 5 | 4 | 5 | 0 | 0 | 100 |
| Forde | 5 | 5 | 5 | 0 | 0 | 100 |
| 2000 | | | | | | |
| Payne | 5 | 5 | 4 | 0 | 0 | 100 |
| Tulare | 5 | 5 | 5 | 0 | 0 | 100 |
| Chandler | 5 | 4 | 4 | 0 | 60 | 40 |
| Sexton | 5 | 5 | 5 | 0 | 0 | 80 |
| Gillet | 5 | 4 | 5 | 0 | 0 | 90 |
| Forde | 5 | 5 | 4 | 0 | 0 | 90 |
| 2001 | | | | | | |
| Payne | 5 | 5 | 5 | 0 | 30 | 70 |
| Tulare | 5 | 5 | 5 | 0 | 0 | 100 |
| Chandler | 4 | 4 | 4 | 0 | 100 | 0 |
| Sexton | 6 | 5 | 5 | 0 | 40 | 60 |
| Gillet | 5 | 4 | 5 | 0 | 0 | 90 |
| Forde | 5 | 5 | 5 | 0 | 0 | 90 |
| 2002 | | | | | | |
| Payne | 5 | 5 | 5 | 0 | 0 | 90 |
| Tulare | 5 | 5 | 5 | 0 | 0 | 100 |
| Chandler | 4 | 4 | 4 | 0 | 100 | 0 |
| Sexton | 6 | 5 | 5 | 0 | 50 | 50 |
| Gillet | 5 | 5 | 5 | 0 | 0 | 100 |
| Forde | 5 | 5 | 4 | 0 | 100 | 0 |
| 2003 | | | | | | |
| Payne | 5 | 5 | 5 | 0 | 0 | 90 |
| Tulare | 6 | 5 | 4 | 10 | 33 | 67 |
| Chandler | 5 | 4 | 4 | 0 | 100 | 0 |
| Sexton | 5 | 5 | 5 | 0 | 40 | 40 |
| Gillet | 5 | 5 | 5 | 0 | 10 | 90 |
| Forde | 5 | 5 | 4 | 0 | 50 | 50 |
| 5 YEAR AVERAGE | | | | | | |
| Payne | 5 | 4.8 | 4.6 | 0 | 16 | 76 |
| Tulare | 5.2 | 5 | 4.6 | 2 | 7 | 93 |
| Chandler | 4.4 | 4.2 | 3.6 | 0 | 90 | 10 |
| Sexton | 5.6 | 5 | 4.8 | 0 | 46 | 48 |
| Gillet | 5 | 4.4 | 5 | 0 | 2 | 94 |
| Forde | 5 | 5.4 | 4.4 | 0 | 30 | 66 |

| | KERNEL | | | | |
|---|---|---|---|---|---|
| | Light amber % | Amber % | Tip shrivel % | Other shrivel % | Veins % |
| 1999 | | | | | |
| Payne | 20 | 0 | 0 | 20 | 30 |
| Tulare | 0 | 0 | 0 | 0 | 0 |
| Chandler | 0 | 0 | 30 | 0 | 0 |
| Sexton | 0 | 0 | 20 | 0 | 0 |
| Gillet | 0 | 0 | 0 | 0 | 0 |
| Forde | 0 | 0 | 0 | 0 | 0 |

TABLE 2-continued

| NUT AND KERNEL TRAITS | | | | | |
|---|---|---|---|---|---|
| 2000 | | | | | |
| Payne | 0 | 0 | 1 | 0 | 30 |
| Tulare | 0 | 0 | 1 | 0 | 0 |
| Chandler | 0 | 0 | 40 | 0 | 0 |
| Sexton | 20 | 0 | 10 | 0 | 10 |
| Gillet | 10 | 0 | 20 | 0 | 20 |
| Forde | 0 | 10 | 10 | 0 | 0 |
| 2001 | | | | | |
| Payne | 0 | 0 | 0 | 0 | 20 |
| Tulare | 0 | 0 | 20 | 0 | 0 |
| Chandler | 0 | 0 | 10 | 0 | 0 |
| Sexton | 0 | 0 | 10 | 0 | 10 |
| Gillet | 10 | 0 | 0 | 0 | 0 |
| Forde | 10 | 0 | 0 | 0 | 0 |
| 2002 | | | | | |
| Payne | 10 | 0 | 0 | 0 | 0 |
| Tulare | 0 | 0 | 0 | 0 | 0 |
| Chandler | 0 | 0 | 40 | 0 | 0 |
| Sexton | 0 | 0 | 0 | 0 | 0 |
| Gillet | 0 | 0 | 0 | 10 | 10 |
| Forde | 0 | 0 | 0 | 0 | 0 |
| 2003 | | | | | |
| Payne | 10 | 0 | 0 | 0 | 10 |
| Tulare | 0 | 0 | 0 | 0 | 0 |
| Chandler | 0 | 0 | 20 | 0 | 0 |
| Sexton | 20 | 0 | 20 | 20 | 0 |
| Gillet | 0 | 0 | 10 | 0 | 0 |
| Forde | 0 | 0 | 10 | 0 | 0 |
| 5 YEAR AVERAGE | | | | | |
| Payne | 8 | 0 | 0.2 | 4 | 18 |
| Tulare | 0 | 0 | 4 | 0 | 0 |
| Chandler | 0 | 0 | 28 | 0 | 0 |
| Sexton | 8 | 0 | 12 | 4 | 4 |
| Gillet | 4 | 0 | 6 | 2 | 6 |
| Forde | 2 | 2 | 4 | 0 | 0 |

KEY FOR TABLE 2

| | |
|---|---|
| Texture | Shell texture: 3 smooth; 5 medium; 7 rough |
| Color | Shell color: 3 light; 5 medium; 7 dark |
| Seal | Shell seal: 3 weak; 5 intermediate; 7 strong |
| Strength | Shell strength: 3 weak; 5 intermediate; 7 strong |
| Integrity | Shell integrity: 3 substantial area of shell missing; 5 small area of missing shell; 6 stem end hole; 7 complete shell |
| Thickness | Shell thickness at mid-cheek in mm |
| Packing tissue | Inner lining: 3 thin; 5 medium; 7 thick |
| Inshell weight | gm |
| Kernel weight | gm |
| Kernel % | Kernel wt/ inshell wt × 100 |
| Fill | Kernel fill: 3 poor; 5 moderate; 7 well |
| Plumpness | Kernel plumpness: 3 thin; 5 moderate; 7 plump |
| Ease of removal | Ease of removal of kernel halves: 3 easy; 5 moderate; 7 difficult |
| Blanks % | Percent of nuts without a kernel |
| Extra light % | Percent of kernels in extra light category (DFA) |
| Light % | Percent of kernels in light category (DFA) |
| Light amber % | Percent of kernels in light amber category (DFA) |
| Amber % | Percent of kernels in amber category (DFA) |
| Tip shrivel % | Percent of kernels with tip shrivel like Chandler |
| Other shrivel % | Percent of kernels with more substantial shrivel |
| Veins % | Percent of kernels with conspicuous veins |

DFA Dried Fruit Association of CA

What we claim is:

1. A new variety of walnut tree substantially as shown and described herein.

* * * * *